(12) United States Patent
Emmert-Buck

(10) Patent No.: US 7,214,477 B1
(45) Date of Patent: May 8, 2007

(54) LAYERED DEVICE WITH CAPTURE REGIONS FOR CELLULAR ANALYSIS

(75) Inventor: Michael R. Emmert-Buck, Silver Spring, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 674 days.

(21) Appl. No.: 10/048,194

(22) PCT Filed: Jul. 26, 2000

(86) PCT No.: PCT/US00/20354

§ 371 (c)(1),
(2), (4) Date: Feb. 15, 2002

(87) PCT Pub. No.: WO01/07915

PCT Pub. Date: Feb. 1, 2001

Related U.S. Application Data

(60) Provisional application No. 60/145,613, filed on Jul. 26, 1999.

(51) Int. Cl.
*C12Q 1/00* (2006.01)

(52) U.S. Cl. .............................. 435/4; 435/6; 435/7.1

(58) Field of Classification Search .................. 435/4, 435/6, 7.1, 7.21; 436/501, 63, 64
See application file for complete search history.

(56) References Cited

U.S. PATENT DOCUMENTS 3,620,947 A    11/1971   Allen et al.

(Continued)

FOREIGN PATENT DOCUMENTS

EP    139379    5/1985

(Continued)

OTHER PUBLICATIONS

Schena, M. et al. Science, 270: 467-470, 1995.*

(Continued)

*Primary Examiner*—Christopher H. Yaen
*Assistant Examiner*—Hong Sang
(74) *Attorney, Agent, or Firm*—Klarquist Sparkman, LLP

(57) ABSTRACT

The present invention involves methods, systems, and devices for analyzing a biological material, such as a cellular or other specimen. The method includes placing the specimen on a substrate having different capture regions, such as contiguous layers, wherein the different capture regions of the substrate contain different identification molecules, and transferring components of the specimen through the capture regions under conditions that allow the components to interact with different identification molecules in the different regions of the substrate. The components of the specimen can be transferred through the different layers (or other regions) of the substrate by capillary action of a solution moving through the cellular specimen or by electrophoresis. The transfer of components of the specimen through the substrate may occur while maintaining a geometric correspondence to the specimen, such as the cytoarchitecture of a cellular specimen, for example by moving the components through parallel layers having positions that correspond to positions within the specimen. When the cellular architecture of the specimen is maintained, a correlation between the different identification molecules and the components of the cellular specimens may be made. The analysis can occur with one or more different discrete (for example cellular) specimens on a surface of the substrate. Examples of cellular specimens include, but are not limited to tissue sections, particularly tumor tissue sections. The cellular specimen can also include cultured cells or a cytology sample. Cytostat tissue sections cut slightly thicker than usual, that is about 25 to about 50 μm, improves the ability to detect molecules of moderate and low level abundance.

57 Claims, 5 Drawing Sheets

U.S. PATENT DOCUMENTS

| | | | |
|---|---|---|---|
| 4,176,069 A | | 11/1979 | Metz et al. |
| 4,337,131 A | | 6/1982 | Vesterberg |
| 4,613,567 A | | 9/1986 | Yasoshima et al. |
| 4,716,101 A | | 12/1987 | Thompson et al. |
| 4,795,562 A | | 1/1989 | Walsh |
| 4,840,714 A | | 6/1989 | Littlehales |
| 4,874,691 A | | 10/1989 | Chandler |
| 5,047,135 A | | 9/1991 | Nieman |
| 5,057,438 A | * | 10/1991 | Imai et al. .................. 436/516 |
| 5,078,853 A | | 1/1992 | Manning et al. |
| 5,155,049 A | | 10/1992 | Kauvar et al. |
| 5,173,159 A | | 12/1992 | Dutertre |
| 5,238,651 A | | 8/1993 | Chuba |
| 5,332,484 A | | 7/1994 | Hilt |
| 5,387,325 A | | 2/1995 | Opplt |
| 5,427,664 A | | 6/1995 | Stoev et al. |
| 5,438,128 A | | 8/1995 | Nieuwkerk et al. |
| 5,486,452 A | | 1/1996 | Gordon et al. |
| 5,650,055 A | | 7/1997 | Margolis |
| 5,679,310 A | | 10/1997 | Manns |
| 5,716,508 A | | 2/1998 | Starr |
| 5,741,639 A | | 4/1998 | Ensing et al. |
| 5,843,657 A | | 12/1998 | Liotta et al. |
| 5,993,627 A | | 11/1999 | Anderson et al. |
| 6,013,165 A | | 1/2000 | Wiktorowicz et al. |
| 6,064,754 A | | 5/2000 | Parekh et al. |
| 6,087,134 A | | 7/2000 | Saunders |
| 6,135,942 A | | 10/2000 | Leptin |
| 6,232,067 B1 | | 5/2001 | Hunkapiller et al. |
| 6,602,661 B1 | * | 8/2003 | Knezevic et al. .............. 435/6 |

FOREIGN PATENT DOCUMENTS

| | | |
|---|---|---|
| EP | 0525723 | 2/1993 |
| WO | WO 98/20353 | 5/1998 |
| WO | WO 98/41863 | 9/1998 |
| WO | WO 99/67647 | 12/1999 |
| WO | WO 00/45168 | 8/2000 |

OTHER PUBLICATIONS

Huang, A.-H. et al., Analytical Biochemistry, 268: 305-317, 1999.*

Okabe et al. J. Histochem. Cytochem. 1993, 41(6): 927-934.*

Pappalardo et al. Seminars in Radiation Oncology, 1998, 8(3): 217-223.*

Cleeve and Tua, "Isoelectric focusing of human tissue alkaline phosphatase isoenzymes in agarose gel," *Clinica Chimica Acta* 137:333-340, 1984.

Englert et al., "Molecular profiling of human cancer: New opportunities," *Curr. Opin. Mol. Therap.* 1(6):712-719, 1999.

Englert et al., "Layered Expression Scanning: Rapid Molecular Profiling of Tumor Samples," *Cancer Res.* 60:1526-1530, Mar. 15, 2000.

Inczedy-Marcsek et al., "Extraction of proteins within ultrathin-layer polyacrylamide electrophoresis (SDS-PAGE) and isoelectric focusing (PAGIF) of cryostat sections and tissue culture specimens," *Acta histochemica, Suppl.-Band XXXVI* S:377-394, 1988.

Schumacher et al., "Direct tissue isoelectric focusing on ultrathin polyacrylamide gels. Applications in enzyme, lectin and immunohistochemistry," *Histochemical Journal* 22:433-438, 1990.

Schumacher and Trudrung, "Direct Tissue Isoelectric Focusing on Mini Ultrathin Polyacrylamide Gels followed by Subsequent Western Blotting, Enzyme Detection, and Lectin Labeling as a Tool for Enzyme Characterization in Histochemistry," *Anal. Biochem.* 194:256-258, 1991.

van der Sluis et al., "Immunochemical detection of peptides and proteins on press-blots after direct tissue gel isoelectric focusing," *Electrophoresis* 9:654-661, 1988.

Braun and Abraham. "Modified diffusion blotting for rapid and efficient protein transfer with PhastSystem," *Electrophoresis* 10:249-253. 1989.

Demczuk et al., "Identification and analysis of all components of a gel retardation assay by combination with immunoblotting." *Proc. Natl. Acad. Sci. USA* 90:2574-2578, Apr. 1993.

Heukeshoven and Dernick, "Effective blotting of ultrathin polyacrylamide gels anchored to a solid matrix," *Electrophoresis* 16:748-756. 1995

Legocki and Verma, "Multiple Immunoreplica Techique: Screening for Specific Proteins with a Series of Different Antibodies Using One Polyacrylamide Gel," *Anal. Biochem.* 111:385-392. 1981.

Manabe et al., "An Electroblotting Apparatus for Multiple Replica Technique and Identification of Human Serum Proteins on Micro Two-Dimensional Gels," *Anal. Biochem.* 143:39-45, 1984.

Neumann and Müllner, "Two replica blotting methods for fast immunological analysis of common proteins in two-dimensional electrophoresis." *Electrophoresis* 19:752-757, 1998.

Olsen and Wiker, "Diffusion blotting for rapid production of multiple identical imprints from sodium dodecyl sulfate polyacrylamide gel electrophoresis on a solid support." *J. Immunol. Methods* 220:77-84, 1998.

Sanchez et al., "Simultaneous analysis of cyclin and oncogene expression using multiple monoclonal antibody immunoblots." *Electrophoresis* 18:638-641, 1997.

* cited by examiner

After transfer through 10 layers

Individual glands, Stromal bands, Urethra

H & E

After transfer through 100 layers

H & E 60 kD–
42 kD–
30 kD–
22 kD–

60 kD–
42 kD–
30 kD–

60 kD–

POV1 Actin

LAYERED DEVICE WITH CAPTURE REGIONS FOR CELLULAR ANALYSIS

CROSS REFERENCE TO RELATED APPLICATIONS

This application is a U.S. National Stage application of International Application No. PCT/US00/20354, filed Jul. 26, 2000, (published in English under PCT Article 21(2)), which in turn claims the benefit of U.S. Provisional Application No. 60/145,613, filed Jul. 26, 1999. Both applications are incorporated herein in their entirety.

FIELD OF THE INVENTION

The present invention is related to the separation and identification of components of cellular specimens. In particular, the present invention involves expression scanning, and in particular examples a method of identifying specimen components while maintaining the spatial relationship between the location of the specimen component of interest and the remainder of the specimen.

BACKGROUND OF THE INVENTION

The Human Genome Project and other gene discovery initiatives are dramatically increasing the information available regarding the number, genomic location, and sequences of human genes. Accompanying the expanding base of genetic knowledge are several new technologies geared toward high-throughput mRNA and proteomic analysis of biological samples, allowing a global view of the genes and gene products that reflect normal physiology and pathological states. Utilized together, the expanding genetic database and newly developing analysis technologies hold tremendous potential to increase the understanding of normal cellular physiology and the molecular alterations that underlie disease states. However, many biological specimens, such as whole cell tissue samples, remain uniquely difficult to analyze due to their complex cellular heterogeneity.

The first report of the application of tissue sections directly onto paper strips and subsequent electrophoresis was made by Lindner et al. (1956). Later, Saravis et al. (1979) utilized agarose gels and Bonte (1978) utilized polyacrylamide gels to achieve better separation of the analyzed proteins. As reported in a review by Neuhoff (1980), routine application of these procedures to whole cell tissues was not widespread because of technical difficulties, so methods using extraction of the proteins from the sample through cell lysis before separation predominated.

More recently, Inczedy-Marcsek et al. (1988) described the use of electrophoresis and isoelectric focusing of cryostat samples placed directly upon ultra thin polyacrylamide gels. The use of ultra thin gels allowed for extraction of the proteins from the tissue sample without lysis of the cells of the sample, and did overcome some of the technical difficulties experienced by early workers in this field. Schumacher et al. (1990) also described the use of isoelectric focusing to identify enzymes, glycoproteins, and neuropeptides present in cryostat sections. This process involved the direct placement of the sample upon ultra thin gels, followed by isoelectric focusing. The processes of both Inczedy-Marcsek et al. and Schumacher et al. produce gels in which the proteins or other molecules of interest move through the gel medium according to physical characteristics related to charge and molecular weight. However, these approaches provide information only on the total molecular content of the sample being analyzed, representing the aggregate proteins and nucleic acids present in all of the various cell types present in the specimen.

Isofocusing and electrophoresis processes have been disclosed for cryostat tissue samples, followed by immunochemical analysis. Specifically, Schumacher and Trudrung (1991) and van der Sluis et al. (1988) describe the identification of alkaline phosphatases and peptides such as vassopressin, respectively, through direct tissue isoelectric focusing followed by Western blotting. This immunochemical analysis technique involves the movement of the protein or molecules of interest, through capillary action, from the focusing gel to nitrocellulose membranes. The membrane-bound protein is then detected using immunostaining procedures. Van der Sluis et al. (1988) did attempt to generally localize the proteins within the tissue sample by applying this procedure to a series of sliced tissue sections. However, the immunodetection process was preceded by an isofocusing step, so the results only indicated presence of the protein within a particular tissue sample.

Molecular analysis of cell populations in tissue sections have been performed using immunohistochemistry (IHC) and in-situ hybridization (ISH). The ISH technique is reviewed by Jin and Lloyd (1997), and the IHC technique is reviewed by Grogan (1992). While these techniques have been valuable tools to investigate the cellular localization of a particular protein or mRNA in a complex tissue section, they both suffer from three major drawbacks. First, IHC and ISH are limited to analysis of a single molecular species per sample. Second, artifact staining based on cross-hybridization severely affects the accuracy of the test results. Finally, these methods have limited ability to visualize proteins and mRNAs expressed at moderate or low levels of abundance.

Techniques have been disclosed for separating particular subsets of cells from a whole tissue sample. For example, Emmert-Buck et al. (1996) describe the use of laser-based microdissection techniques to rapidly procure microscopic, histopathologically defined cell populations. Alternatively, tissue arrays, such as those described by Kononen et al. (1998) permit individual molecules to be studied simultaneously in hundreds of separate tissue samples. However, there remains a need in the art for an improved method of analyzing proteins or other molecules of interest present in cellular specimens where the method is capable in some embodiments of providing information concerning the location of the proteins or molecules of interest in the initial tissue sample, and/or provide a method that avoids some of the problems encountered with IHC and ISH.

SUMMARY OF THE DISCLOSURE

The present disclosure describes methods, systems, and devices for analyzing a biological specimen, such as a cellular specimen. The method includes placing the specimen on a substrate with capture regions, such as matrices or layers, wherein the different regions of the substrate contain different identification molecules, and transferring components of the specimen through the regions under conditions that allow the components to interact with different identification molecules in the different regions (such as contiguous layers) of the substrate. In one embodiment, components of the cellular specimen are transferred through the substrate (such as different matrices or layers of a substrate) by electrophoresis, or by capillary action of a transfer buffer moving through the cellular specimen. In specific examples, the components are transferred sequentially through a plurality of substantially parallel layers.

The transfer of components of a cellular specimen through the substrate can occur while maintaining the cellular architecture of the specimen, if desired. Because the cellular architecture of the specimen may be maintained in some embodiments, a correlation can be established between the location of the different identification molecules interacting with the cellular components, and the original location of the cellular components within the cellular specimens. The analysis can be performed with one or more different discrete cellular specimens on a surface of the substrate. Examples of cellular specimens include, but are not limited to, tissue sections (particularly tumor tissue sections), a cytology sample, microdissected cells and cultured cells. Cytostat tissue sections cut slightly thicker than usual, that is about 25 to about 50 µm, improve the detection of molecules of moderate and low level abundance.

The regions (such as matrices or layers) of the substrate can range from about 1 to more than a hundred, for example several hundred, several thousand, or several tens of thousands in number, with each region (such as a layer) having a thickness (for example) of at least about 25 nm. In particular embodiments, the regions may extend across the substrate (as in layers), and components of the specimen are transferred generally transverse to the layers, but they may be transferred substantially parallel or at other angles to the layers. Identification molecules present in the substrate layers may, for example, be antibodies that interact with the components of the cellular specimen, and can be used to identify particular molecules of interest present in the specimen. Other representative, non-limiting examples of identification molecules include nucleic acids, peptides, receptors, and ligands. The identification molecule can, for example, comprise a capture molecule that retains a component of the specimen in the layer. If this is done, the analysis can be completed by exposing the identification molecule to a detection molecule that associates with a combination of the capture molecule and the component of the sample, or associates with a region of the component different than the region that was recognized by the identification molecule. For example, the molecule of interest can be a protein, and the identification molecule can recognize a first domain of the protein, and the detection molecule recognizes a second domain of the protein.

Another particular embodiment is a method of analyzing a specimen by providing a substrate that includes different regions (such as layers) having contiguous faces, each layer including a corresponding capture molecule capable of interacting with and capturing a component of the specimen; applying the specimen to a face of the substrate, and transferring components (such as intact components) of the specimen through the contiguous faces of the different layers of the matrix. The components of the specimen react with the capture molecule and the pattern of capture in the different layers can be correlated with information about the specimen. For example, interaction with a specific antibody in a particular layer indicates the presence of the antigen in the specimen. The location of the interaction in a layer can be correlated with a position of the specimen. In the instance of cellular specimens, the cellular architecture of a tissue specimen from which the specimen was taken may be preserved, to permit a correlation between the pattern of capture and a cellular or sub-cellular component of the specimen.

The capture molecule used in some embodiments of the present invention has the ability to inhibit the transfer of at least some of one or more molecules of interest present in the specimen to a downstream region (such as a layer) of the substrate. In some embodiments the method results in a pattern of capture that can be viewed as a plurality of two-dimensional patterns that, when stacked, forms a three-dimensional matrix. The two-dimensional patterns may, in specific embodiments, be cytocoherent, in that the patterns reflect the pattern of expression or presence of the molecule of interest within the specimen. When the specimen is a cellular specimen, and the two dimensional patterns are cytocoherent, the third dimensional matrix of capture can be correlated to specific cellular architecture in a cellular specimen. Since the presence of proteins or mRNA are associated with expression of certain gene products, the scan can in some embodiments be referred to as an expression scan.

Another embodiment of the invention includes a device for analyzing a specimen, where that device includes a substrate containing different regions (such as matrices or layers) having a surface to which the specimen may be applied and maintained in a spatial coherence, such as cytocoherence. In such examples, successive regions (such as layers of the substrate) contain different identification molecules, each of which is capable of interacting with and retaining a corresponding intact component of the specimen, even when the cellular specimen has not undergone previous proteolytic, nucleolytic or other degradation prior to transfer through the substrate layers. The device can have substrate layers that are contiguous and conductive, and are capable of transferring intact components of the cellular specimen through the layers, while maintaining a correspondence between a position on a surface of the substrate and a position in the substrate to which the component is transferred. Alternatively, the layers may be separated (particularly when the components are transferred by electrophoresis).

In particular examples, the substrate is structured to be capable of exerting capillary pressure on the specimen to transfer the component through the substrate, where an example of such a structure is a stack of nitrocellulose membranes. If movement by electrophoresis is desired, the device includes electrodes positioned in relationship to the substrate to introduce an electrical current through the substrate, for example through the different layers of a substrate. In such an embodiment, the electrical current moves the components of interest from the specimen through one or more layers of the substrate. If movement by means of a fluid pressure differential is utilized, the device includes a means for establishing and maintaining a fluid pressure differential across the substrate layers.

In another aspect, certain embodiments also include a system for the molecular analysis of a biological sample, such as a cellular specimen. The system may, for example, contain a sample support, multiple contiguous separation regions (such as matrices or layers), a transport means, and at least two housings. The sample support is capable of holding the sample during the movement of a component of the sample from the sample through separation regions. The separation regions may, for example, be aligned (for example stacked) face to face and each region (e.g. matrix or layer) includes capture molecules that are capable of hybridizing to one or more components of the sample. The transport means of the present system can move at least one component of the sample from the sample support, through the faces, and into the separation matrices. The transport means can include, for example, capillary action, a fluid pressure differential, or a pair of electrodes that create an electrical current through the matrices.

An example of a specific housing of the present system holds multiple separation matrices in face to face alignment during the movement of the sample components, but allows for separation of the multiple separation matrices from each other so further analysis can be performed. The second housing is the location for the further analysis of the hybridization between the capture molecule and the component of interest of the cellular specimen.

The foregoing and other objects, features, and advantages of the invention will become more apparent from the following detailed description of several embodiments which proceeds with reference to the accompanying figures. The inclusions of particular embodiment examples in this Summary does not imply that there are essential to the invention.

DETAILED DESCRIPTION OF SEVERAL EMBODIMENTS

This detailed description discloses a method of placing a cellular specimen on a substrate with capture regions, which are identifiable sub-divisions of the substrate, wherein the different regions of the substrate contain different identification molecules, and transferring components of the cellular specimen through the regions under conditions that allow the components to interact with different identification molecules in the different regions of the substrate. The different regions can take a variety of forms, such as separately identifiable substrate sub-units, including a matrix in which the identification molecules are suspended or attached. A matrix is not necessarily a regular array, but instead refers to a unit having a relatively shallow depth, and a face with width and length. The face of the matrix can be parallel, transverse, or at some other angle to a direction of movement of the sample through the substrate. The matrix may extend completely or partially across the substrate, and the different matrices may be of substantially uniform or different dimensions (such as width and length and depth). An example of a particular matrix is a layer, which is one of a series of discrete thin strata which may or may not be separable from one another. Although it should be clear that the substrate can take many different forms, for purposes of illustration, the substrate will be described in association with a layered substrate in which the layers may be physically separated from one another.

Figures 1, 2A, 2B:
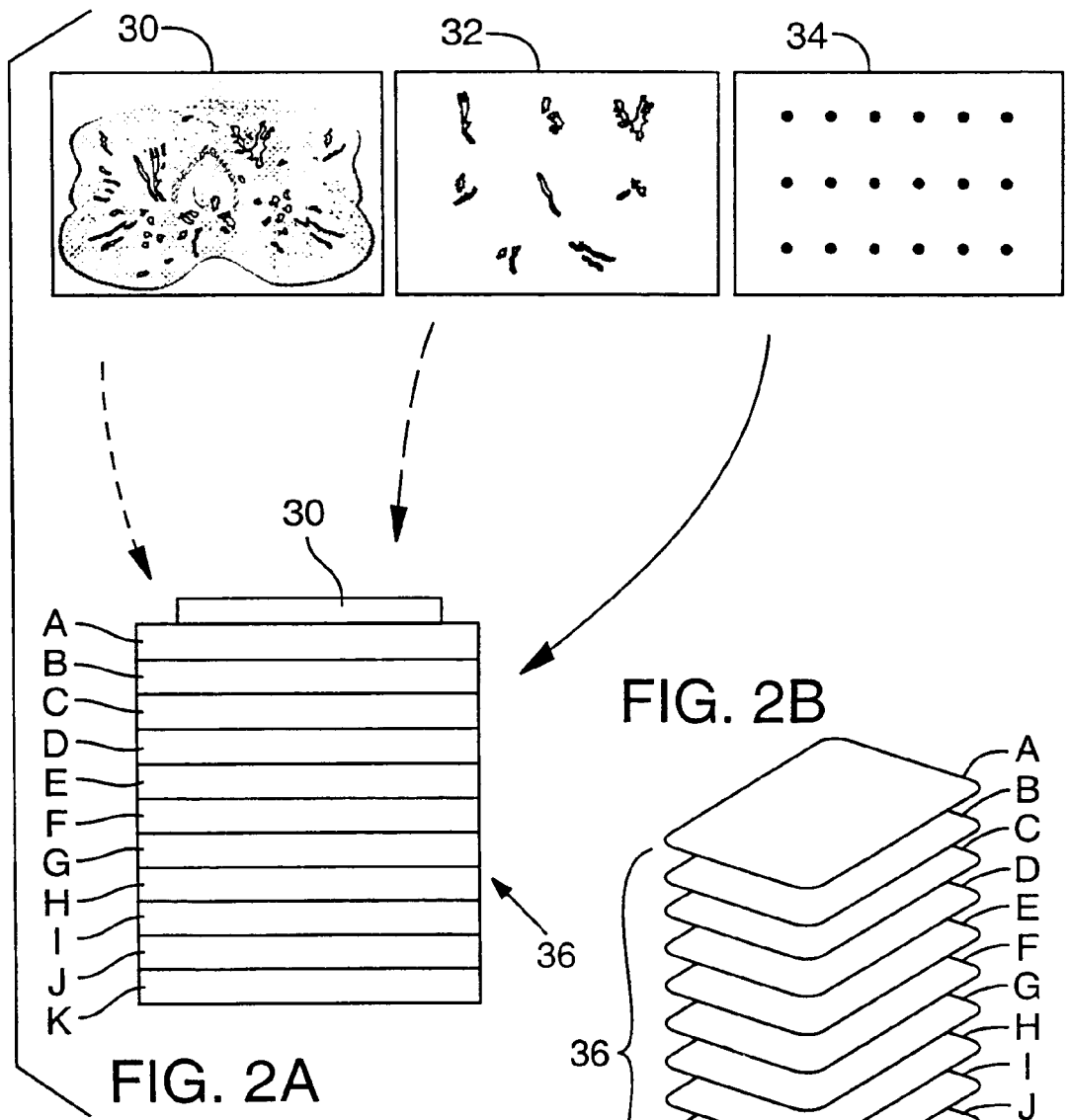
FIG. 1 is an illustration of a prostate section, showing how different areas of the prostate, and different cell populations, can be targeted for analysis, using the present invention. In this particular embodiment, the method is called Layered Expression Scanning (LES).
FIG. 2A is a schematic drawing of the method of the present invention. Three different types of starting specimens are shown: a whole mount tissue specimen; dissected, intact cells; and dissected, lysed cells. This FIG. 2A also includes an enlarged, perspective view of an example of a substrate of the present invention having multiple contiguous porous layers, each layer having a different identification molecule bound within it.
FIG. 2B shows an embodiment of the substrate, similar to that shown in FIG. 2A, but wherein the individual layers are separated.

In this particularly discussed embodiment, biological specimens (such as tissue sections or other cell populations, which are referred to herein as cellular specimens) are separated into multiple layered substrates, such that each of the layers can be subjected to a separate analysis that can be correlated with the cytological architecture of the original specimen. The prostate tissue section of FIG. 1 illustrates how intact tissue sections may have different microscopic variations, which can be usefully correlated with the results of the different analyses. FIG. 1 shows a section of prostate tissue, having an area 1 of lymphocytes not associated with tumor; area 2 of normal epithelium, adjacent to tumor; area 3 of low grade tumor; area 4 of stroma; area 5 of high grade tumor; area 6 of hyperplasia; area 7 of low grade prostatic intraepithelial neoplasia (PIN); area 8 of normal epithelium, not adjacent to tumor; and area 9 of lymphocytes, associated with tumor. It is of interest to be able to determine different molecular characteristics of the intact tissue specimen, and correlate those molecular characteristics with particular regions of the tissue. Particular embodiments of the layered expression scans (LES) of the present invention make this possible.

One example of a layered expression scan is shown in schematic form in FIG. 2. One or more biological samples, such as an intact tissue section (for example prostate section 30), dissected intact cell lysates 32, or dissected cell lysates 34, are prepared and placed within or upon an ultra thin gel, called a sample gel, which is applied to a multilayered gel, for example to a surface (such as a top surface) of a multilayered substrate 36.

The sample gel can utilize any known gel matrix including agarose, polyacrylamide and gelatin based matrices. If the sample gel is agarose, its concentration is, for example, in the range of about 0.1% to about 5%, and it may be cast to be "ultrathin," that is, in the range of about 0.10 µm to about 1 mm thick. Alternatively, the biological samples can be placed directly in the substrate or on a surface, such as the top surface, of the multilayered substrate 36. For purposes of simplified illustration in FIG. 2, the intact prostate section 30 is placed directly on a top surface of the multi-layered substrate 36.

The specimen 30 is placed on the top surface of the substrate layer A, which surface is substantially parallel to separations between the layers. For purposes of illustration, eleven layers are shown (although many more can be used, for example at least hundreds or thousands of layers), and the layers are labeled A through K. Each of the layers may be a membrane or film, each of which may contain one (or more) identification molecules, such as an antibody that recognizes a particular antigen, or a DNA sequence that functions as a probe by hybridizing to complementary DNA sequences in the specimen. The identification molecule can be different in each of the layers A–K or the same.

After application of the specimen 30 to the flat top surface of layer A, the soluble contents of the specimen are transferred (for example by capillary action or electrophoresis) through the series of layers A–K, while maintaining the overall two-dimensional architecture within the sample. As the specimen components, such as proteins and nucleic acids, pass through the membranes, the identification molecules of the substrate layers interact with the proteins or molecules of interest. After this interaction occurs, the membranes are separated (FIG. 2B) and subjected to further analysis, such as exposure to a second antibody or DNA sequence, producing a highly sensitive and specific molecular profile, or "expression scan" of the cellular specimen. If the analysis is applied to a whole tissue specimen, the final step of the method can involve examination of a reference specimen cut from a location immediately adjacent to the first tissue specimen, so that areas of interest in the intact specimen (such as areas of cellular atypia) can be correlated with findings in the expression scan. In this manner, molecular characteristics of the specimen (such as the expression of particular proteins) can be correlated with areas of histological interest (such as invasion of the prostate capsule). In the context of this example, expression of particular proteins associated with capsular invasion (or metastasis in general) can be located.

The present example of analyzing a cellular specimen includes placing the cellular specimen on a layered substrate, where the different layers of the substrate contain different identification molecules, and transferring components of the cellular specimen through the layers under conditions that allow the components to interact with different identification molecules in the different contiguous layers of the substrate. Cellular specimens include, but are not limited to, tissue sections, cultured cells, or a cytology sample. Tumor tissue sections produced by the cryostat method are particularly suited for use in the present method. Standard methods of preparing tissue sections are taught in Lefkovits et al. (1996). If the molecule of interest is present at moderate or low level abundance, such as those present in the range of one to 10,000 copies per cell or even one to 100 copies per cell, the thickness of the tissue section to be analyzed can be increased to intensify the expression scan produced. The thickness of such samples are about 25 µm to about 50 µm. Since an adjacent reference specimen may be used to view the tissue microscopically, and the sections are thin, the histological detail of the analysis is not compromised by utilizing the thicker tissue section for the present method.

The cellular specimen to be analyzed by the method of the present invention may also be obtained by dissecting a cell population of interest from a larger cell population, for example, through laser capture microdissection, or the cellular specimen can be lysates of a dissected cell population. Methods of preparing tissue samples for microdissection are disclosed in Emmert-Buck et al. (1996) and Bonner et al. (1997). The laser capture microdissection procedure, described by Emmert-Buck et al. (1996) and Bonner et al. (1997) allows dissection of particular cell populations of interest from a tissue sample, providing individual samples for experiments that compare the contents of various tissue types within one specimen. FIG. 1 illustrates a tissue sample containing nine populations of interest, where each could be separately isolated using the laser capture microdissection process. Alternatively, comparisons of the same tissue over time, such as changes in protein expression or mRNA during tumor development, can be obtained. If an investigator wishes to study a protein or mRNA of very low abundance, such as menin, the gene responsible for Multiple Endocrine Neoplasia Type 1, then preparation of a highly concentrated lysate derived from microdissected cells can be utilized. Very low abundance mRNA would be present in the cell in a range of one to 10,000 copies. It is also possible to amplify low abundance mRNAs by reverse transcription/polymerase chain reaction (RT/PCR) and then analyze for their corresponding cDNAs.

As previously discussed, the prepared cellular specimen is optionally placed in a gel, to allow ease of handling prior to analysis. In some embodiments, the sample gel may be an ultra thin gel made of agarose or polyacrylamide. The sample gel could be made using standard 2% agarose dissolved in tris-borate EDTA buffer. Two hundred µl of this preparation is pipetted onto a standard glass histology slide and coverslipped, thus creating an ultrathin gel on the order of 0.5–1 mm thick. The sample gel can be selected to participate in separating the different components of the cellular specimen. This separation function is accomplished by providing the sample gel with a particular structure that alters or aids the migration of certain components into the layers of substrate 36, and/or retards the migration of components that should remain in the sample gel. Structural changes that aid the separation function include varying the gel concentration to alter the gel pore size, or varying gel composition, such as using an acidic or basic formulation to aid or retard the migration of certain components. If no separation function by the sample gel is desired, a gel with neutral characteristics can be chosen, such as 2% agarose in TBE with a pH of 7.4.

If no gel separation function is desired and the physical form of the sample is appropriate (for example a tissue section), the specimen 30 is placed directly on a planar top face of the first layer A (FIG. 2A) of the substrate 36. Even if a gel is not used, the analyzed cellular specimen can be treated before transfer to allow selective transfer of certain target molecules into the substrate layers. An example of such a treatment is the use of a transfer buffer that contains detergents, which would tend to increase the transfer of components of a cellular specimen that are present in the cellular membrane (such as the plasma membrane).

If the samples are solubilized cellular lysates, purified proteins, or nucleic acids, it is possible to prepare a sample gel as follows. A 2 mm thick 2% agarose gel is "punched" to generate a series of holes (4 mm in diameter, for example) that serve as sample "wells." The samples may then be added to 1% liquid agarose, placed into the wells, and then allowed to solidify to form a sample gel 34. The sample gel created by this process may then be placed on top of the layered substrate 36.

The layered substrate 36 of the embodiment disclosed in FIG. 2A includes separable layers of a material (such as layers A–K of nitrocellulose, which can be obtained from Schleicher and Schuell, Keene, N.H., product #BA-85) which is capable of placement in multiple contiguous layers, as shown in FIG. 2A, and subsequent separation into multiple separate (non-contiguous) layers, as shown in FIG. 2B. The nitrocellulose layers may be treated with a blocking agent, to inhibit binding of proteins to the nitrocellulose of the layers, which allows proteins to pass through the layer unless it interacts with and is captured by the identification molecule. Once the components of the specimen have migrated through the contiguous layers, the layers are separated to permit individualized analysis of the components of the cellular specimen retained in each separated layer.

Other examples of the substrate layers include, but are not limited to high concentration agarose gels, low concentration agarose gels, high concentration polyacrylamide gels, a low concentration polyacrylamide gel, and membranes, such as porous membranes like nitrocellulose paper. Low concentration agarose is from about 0.1 to about 3%, while high concentration is above about 3%. Low concentration acrylamide is about 2% to about 20%, while high concentration is above about 20%. Such gels or membranes may optionally be backed with a polyester membrane or the like to provide mechanical strength and to provide a "contact substance" that permits efficient transfer of the components of the cellular specimen between the layers of the substrate and reduces loss of the two-dimensional architecture of the sample (such as sample 30) as the components migrate through the substrate 36.

Nitrocellulose layers are examples of porous layers, that exert capillary pressure on the specimens (such as specimen 34) on the top surface of layer A (FIG. 2A), and conduct components of the specimens through the layers. Such porous layers or membranes allow the movement of liquid from one face to an opposite face of the membrane, and exert capillary action on the specimen to move soluble components of the specimen through the multiple layers. The pore size of the porous layers may be any that are available, particularly the about 0.45 μm pore-size nitrocellulose membrane. The number of layers in the substrate can vary widely, for example from about 1 to at least 2, 5, 10 or even 1000 layers, although for purposes of illustration eleven layers A through K are shown in FIGS. 2A and 2B. The number of layers can be varied, depending in part on the number of different binding or other identification molecules being used, and is ultimately limited only by the ability to promote migration of the cellular components through the substrate levels. The substrate layers can be of identical structure, or the layers can be mixtures of different substrate types.

In a disclosed embodiment, each layer (or other type of region) of the substrate is impregnated with multiple copies of at least one identification molecule that can interact with one or more molecules of interest. Similarly, different layers of the substrate can contain multiple different identification molecules, for example each layer (or other type of region) can have one or more identification molecules present. In an alternative embodiment of the substrate, all the layers (or other type of region) would contain the same identification molecule and differential migration through the various substrate layers would allow separation. The differential migration can be promoted by differing physical characteristics of the substrate layers, such as different pore diameters or pH, or porosity or pH gradients, in the direction of layers A to K. Likewise, in other embodiments, some of the substrate layers do not contain identification molecules and may serve to promote differential migration of sample components through the layers.

Representative examples of identification molecules include, but are not limited to antibodies, nucleic acids, peptides, receptors, ligands, dyes, stains, or colorimetric enzymes. Specific examples of identification molecules include anti-prostate specific antigen antibodies (Scripps, San Diego, Calif.; anti-cytokeratin antibodies, anti-alpha-actin antibodies (Sigma, St. Louis, Mo.); anti-PB39 antibodies, and anti-menin antibodies (National Cancer Institute Core Antibody Lab, Fredrick, Md.). Identification molecules can interact specifically with the molecule of interest, such as the binding of an antibody or complementary interaction with a single stranded DNA sequence, or more generally, such as the interaction between a dye and a molecule colored by that dye. If the identification molecule prevents the migration of the molecule of interest into subsequent layers of the substrate, the identification molecule is referred to as a capture molecule.

When the transfer of the components of the cellular specimen occurs through capillary movement of liquid present in the sample through the substrate, it is desirable to have the multiple layers (or other regions) of the substrate in physical contact with each other. The use of contiguous substrate layers A–K (as in FIG. 2A) reduces the effects of diffusion on the accurate migration of the proteins or molecules of interest through the substrate and enhances the capillary movement of the components. Alternatively, the components can be moved through the substrate layers (or other regions) using electrophoresis, a variation of isoelectric focusing, or other similar methods of moving charged molecules. If electrophoresis or another method using electricity is used, the different layers of the substrate are ideally conductive, such as an agarose or polyacrylamide gel. Methods based on electrophoresis would be limited generally to separation of charged species from the cellular specimen. However, the use of electrophoresis can avoid the use of contiguous substrate layers. For example, the layers could be separated from one another, as long there is an electrically conductive medium (such as a liquid, particularly a liquid comprising ions, such as may be formed by dissolving a salt in a liquid) between the layers through which the specimen is electrophoresed.

Another means of transferring sample components through the substrate layers (or other regions) is by way of liquid movement in response to a fluid pressure differential. For example, pressure, such as provided by a compressed gas, may be applied to the sample to force the liquid present in the sample into and through the substrate 36. Alternatively, another liquid under pressure may be used to carry sample constituents into and through the substrate layers to an area of lower pressure. Liquid present in a sample or provided to carry sample constituents into the substrate layers may also be induced to move through the substrate 36 by a vacuum applied to the substrate 36 opposite the surface where the sample (such as sample 30) is applied. Since a continuous fluid medium can be established with such an approach, the layers can be either contiguous or non-contiguous.

After the molecules of interest have been transferred through the substrate layers in the disclosed example, the various layers can be separated from each other to allow analysis using a second identification molecule, separate from that used for initial capture, such as a second antibody or DNA sequence. For example, the second antibody can be a specific binding agent such as an antibody that recognizes the original antibody bound to its antigen in the substrate layer. The use of the second identification agent ensures high specificity of the staining signal present in the expression scan.

Separate analysis of different substrate layers is illustrated in FIGS. 2A–B. In this example, a whole mount section of human prostate tissue, representing a cross section of the entire organ, was placed on top of the substrate and transferred through ten capture layers, and onto a nitrocellulose membrane. The membrane was subsequently processed similar to a standard immunoblot using an antibody against cytokeratin, which selectively stains epithelium.

Figure 3A:
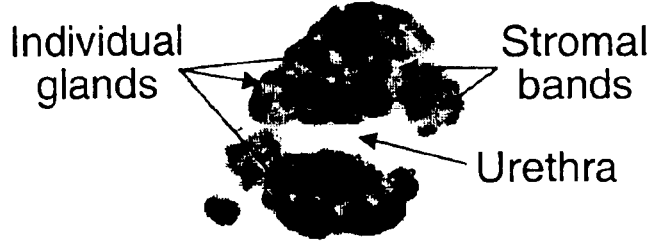
FIG. 3 presents a set of photomicrographs that illustrate retention of the two-dimensional architecture of a whole mount tissue sample during transfer through multiple capture layers. The figures show an intact section of prostate tissue (FIG. 3B) and an image after (FIG. 3A) capillary transfer through capture membrane layers, each layer having a different type of antibody bound throughout it. The whole mount section of human prostate represents a cross section of the entire organ, which was placed on a top layer of ten capture layers, then transferred through the layers and on to a nitrocellulose membrane. The membrane was subsequently processed similar to a standard immunoblot, using an antibody against cytokeratin, which selectively stains epithelium (FIG. 3A). Retention of the basic organization of the tissue section throughout the transfer process is demonstrated by comparing FIG. 3A with FIG. 3B, which is a hematoxylin and eosin stained slide of an adjacent recut from the same tissue block. Retention of tissue section architecture after transfer through 100 capture layers is also demonstrated by comparing FIG. 3C with FIG. 3D, which show, respectively, the anti-cytokeratin antibody stained nitrocellulose layer obtained after transfer of a whole mount tissue section through 100 layers and a hematoxylin and eosin stained slide of an adjacent recut from the same tissue block.
Figure 3B:
Figure 3C:
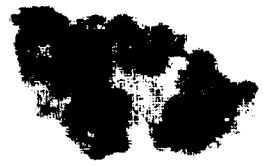
Figure 3D:

Retention of the basic organization of the tissue section throughout the transfer process is demonstrated by comparing FIG. 3A (cytokeratin antibody transfer layer) with FIG. 3B (hematoxylin and eosin stained slide of an adjacent recut from the same tissue block).

The specificity of molecular capture using this technique was also illustrated by transferring a whole mount section of prostate tissue through ten capture membranes, each having a different antibody linked throughout the membrane. After transfer of the tissue section, each membrane was placed into denaturing buffer to remove captured molecules, and subsequently analyzed by immunoblot using anti-PSA (prostate specific antigen). Specific capture of PSA was demonstrated by isolation of a single PSA band of 30 kDa following electrophoresis.

To demonstrate the potential of the method for very high throughput analysis, a repeat of the PSA capture experiment was performed, except the tissue was transferred through 100 capture layers, with anti-PSA placed on layer #100. Successful capture of PSA in layer #100 was achieved. There does not appear to be a limit to the number of capture membranes which can be utilized, hence the method can include expression scanning using hundreds or even thousands of layers, to allow for simultaneous measurement of thousands of molecular species.

To demonstrate the use of the scanning technique with microdissected samples, nine separate cell populations from three different subjects were procured from tissue sections by laser capture microdissection, solubilized, and transferred as nine separate, 5 mm spots, through ten capture layers, in which polyclonal anti-PSA was present on layer #10. A dissected cell population of prostate epithelial cells was placed in the upper left corner of the top layer of the substrate. After tissue transfer, layer #10 was probed with monoclonal antibody against PSA, and visualized by enhanced chemiluminesence (ECL). Specific PSA staining was visualized only for the tissue sample containing prostate epithelium, consistent with the known epithelial localization of PSA. Samples 2–9 were appropriately negative for PSA staining.

The maintenance of cellular architecture helps determine associations between cellular findings and molecular characteristics determined by the expression scan. For example, the presence of the lymphocytes can be correlated with findings associated with other of the layers. Also, expression of a particular receptor may be correlated or mapped to epithelium. Alternatively, another molecular marker can be associated with areas of metaplasia or capsular invasion.

Separate analysis of the substrate layers allows one to investigate multiple regions of the molecule of interest, i.e., domains of a protein or exons of a RNA transcript, as described more fully in the Examples. The present method can provide a quantitative indication of the relative abundance of the components in the cellular specimen when the identification molecules interact in relative abundance to the quantity of the component of interest in the cellular specimen. Mass spectroscopy sequencing can also be performed after separation to characterize a captured amino acid sequence.

The foregoing explanation will be better illustrated by the following additional specific examples.

EXAMPLE 1

Identification of PSA, Tubulin, Actin, and Cytokeratin in Prostate Tumor

The LES procedure was performed on prostate tumor sections. The preliminary experiment used cytokeratin as the protein of interest. A whole mount cryostat section of human prostate tissue was prepared by making a thin frozen section of prostate, the section having a thickness of about 10 µm. As shown in FIG. 1, the section includes multiple cell populations of biological interest including normal epithelium, pre-malignant lesions, high and low grade tumor foci, and significant tumor-host interactions such as lymphocytes interacting with cancer cells. This section was placed on an ultrathin 2% agarose gel that had been cast on a glass histology slide. The section was covered with 2% agarose solution. A cover slip was applied on top of the section and the agarose was allowed to polymerize, thus creating a two-layered sample gel with the tissue section in between. The agarose sample gel containing the tissue sample was applied to the surface of a single layer substrate made of a 1.75"×1.75" 0.45 pore size nitrocellulose membrane (Schliecher and Schuell, Keen, N.H.). The membrane was then probed with an antibody against cytokeratin (Sigma, 1:1000 dilution) overnight at 4° C. This membrane was then probed a second time with a biotinylated secondary antibody (Sigma, 1:5000 titer) for 30 minutes at room temperature. The membranes were visualized by autoradiography using enhanced chemiluminescence (ECL) as recommended by the manufacturer (Pierce, Rockford, Ill.).

A second experiment to test the specificity of "capture molecules" in the membrane layers was then performed. A 20 µm cryostat section of prostate tissue was prepared within an ultrathin 2% agarose gel as described above. Components of this tissue section as transferred overnight at room temperature through ten contiguous nitrocellulose membranes (0.5"×0.5," 0.45 pore size, Schliecher and Schuell) by capillary action. Prior to use, each membrane was linked to a different identification molecule, in this case, antibodies, for 1 hour at room temperature. The membranes were washed 3 times for 10 minutes in 1×PBS, and treated with a commercial blocking agent (Pierce) for 1 hour at room temperature, followed by a repeat wash. The nitrocellulose/antibody membranes (illustrated as A–J in FIG. 2) were prepared as follows:

| Layer | Identification Molecule | Source |
|-------|------------------------|--------|
| A | Anti-PB39, 644 | NCI |
| B | Anti-actin | Sigma |
| C | Anti-tubulin | Sigma |
| D | Anti-PB39, 655 | NCI |
| E | Polyclonal anti-PSA | Scirpps, San Diego, CA |
| F | Anti-CAIR 1 | NCI |
| G | Anti-PB-39, 656 | NCI |
| H | Anti-cytokeratin | Sigma |
| I | Anti-CD-3 | NCI |
| J | Anti-PB-39, 645 | NCI |

Antibodies were linked to the nitrocellulose membranes according well known procedures such as those disclosed in U.S. Pat. No. 4,774,177, issued to Marks on Sep. 27, 1988 or U.S. Pat. No. 4,727,037, issued to Ring on Feb. 23, 1988, the disclosures of which are hereby incorporated by reference.

Nitrocellulose layers are examples of porous layers that exert capillary pressure on the specimens on the top surface of the substrate, and conduct components of the specimens through the layers. Such porous layers or membranes allow the movement of liquid from one face to an opposite face of the membrane, and exert capillary action on the specimen to move soluble components of the specimen through the multiple layers. Although nitrocellulose avidly binds biomolecules such as proteins, the nitrocellulose can be altered with well known blocking agents to inhibit e.g. protein binding, and promote movement of the protein or other biomolecule through the nitrocellulose layers.

Blocking agents serve to prevent non-specific interactions between the substrate and the components of the sample as they are transferred through the substrate. "Blocking agent" is a collective term for various additives that prevent non-specific binding, but that have no active part in the specific reaction, such as an immunochemical reaction, between a particular identification molecule and its target. Blocking agents are most commonly concentrated protein solutions. Examples of such solutions include 10–20% fetal calf serum and 5% non-fat dry milk powder dissolved in a buffer such as PBS, TBS, or TBST. Commercially available blocking agents include SuperBlock™, Blocker™ BLOTTO, Blocker™ BSA, and SeaBlock™ (Pierce Chemical, Rockford Ill.) as well as NAP-SureBlocker™, a non-animal protein blocking agent (Geno Technology, Maplewood, Mo.).

After transfer, each membrane was separately placed into 30 μl of SDS sample buffer (Novex, San Diego, Calif.) to remove any captured molecules. The removed, solubilized molecules were separated by electrophoresis on a 4–20% tris-glycine acrylamide gel (Novex) for 1.5 hr at 110V. The proteins were transferred to a 0.2 μm pore size PVDF membrane for 2 hours at 40V and analyzed by a standard immunoblotting procedure using a 1:1000 titer of monoclonal anti-PSA molecules (Scripps). In each case, the signal obtained was restricted to the appropriately sized molecular weight band for the molecule captured by the antibody.

The feasibility of transfer through 100 membrane layers was shown by repeating the experiment above with 99 layers treated only with blocking agent and a final layer 100, that had polyclonal anti-PSA antibody linked to its surface. The Western blot showed capture of PSA only in layer 100. Nonspecific capture of PSA in layers 1–99 is avoided by the blocking agent pre-treatment. This experiment was repeated using an antibody against matrix metalloproeinase-2 in layer 100. Instead of Western immunoblotting, the isolated protein was analyzed by gel zymography, as disclosed in Zucker et al. (1994). Thus, it is possible for to allow simultaneous measurement of thousands of molecular species present in the tissue samples or isolated cell populations, through the use of thousands of substrate layers.

Figure 6:
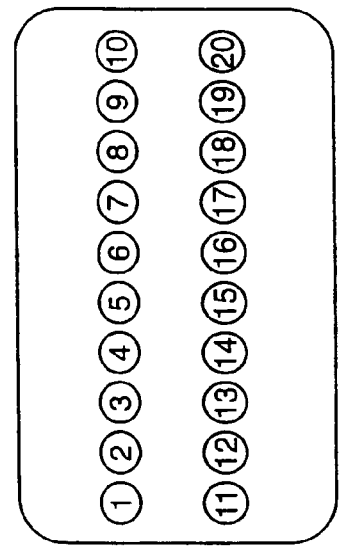
FIG. 6 is a schematic drawing which shows an initial gel with twenty different samples which are passed through ten layers (A through J), and the PSA staining pattern on the tenth layer.
Figure 6:
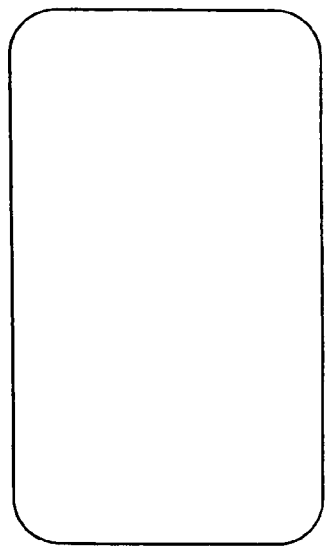
Figure 6:
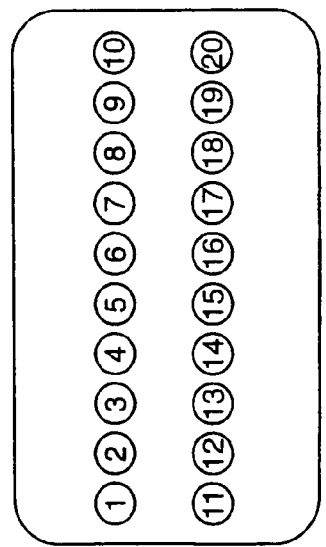

A further experiment was done to detect the presence of PSA in a dissected cell population. Different cell populations, distinguished by tissue type, are separately collected using laser microdissection techniques as described by Emmert-Buck et al. (1997). Ten epithelium samples 1–10 were placed in a row on a sample gel, as shown in FIG. 6, and ten non-epithelium samples 11–20 were placed in a second row immediately below the epithelial samples. All twenty samples were transferred through a substrate containing ten nitrocellulose membranes (A through J), in which only membrane J had anti-PSA antibodies linked to its surface. After transfer, each of the ten membranes was probed with a monoclonal antibody against PSA and visualized by enhanced chemiluminescence (ECL) as described above. The first nine membranes A through I did not produce an ECL signal, indicating no capture of PSA had occurred. However, positive staining for PSA was visualized on membrane J in all of the samples containing epithelium (sample numbers 1–10). This result is consistent with the known epithelial localization of PSA. Samples 11–20 did not contain epithelial cells and were appropriately negative for PSA staining.

EXAMPLE 2

Selective Capture of Prostate Specific Antigen (PSA)

Figure 4A:
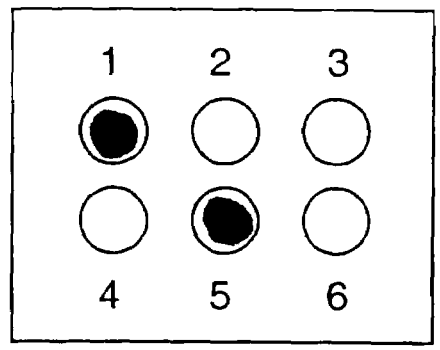
FIG. 4A is a diagram illustrating the staining pattern obtained in a capture layer linked to anti-PSA antibody after five cell lysate samples (only one of which contains PSA) and a positive control of purified PSA were passed as discrete 4 mm spots through ten capture membranes, each capture membrane being linked to a different antibody.

To demonstrate selective molecular capture within substrate layers, cell samples from five separate patients were procured from tissue specimens and solubilized in standard protein extraction buffer. The samples included lysates of normal lung, lung cancer, esophageal cancer, normal prostate, and breast cancer tissue. Each of the cell lysates was placed within a discrete 4 mm diameter spot on the top layer of a capture membrane set. This was accomplished by punching 4 mm diameter holes ("wells") in a 2 mm thick agarose gel, adding the lysates to 1% liquid agarose, filling the 4 mm wells with the lysate/agarose solution, and allowing them to solidify. The sample gel thus created was placed on the top layer of a capture membrane set. Additionally, purified PSA was used as a positive control sample. In this experiment, the capture membranes consisted of ten nitrocellulose layers, each coupled to a different antibody. Polyclonal anti-PSA was linked to layer number ten (the tenth successive capture membrane). The six tissue samples were placed on the surface of the substrate and transferred through the capture membranes by capillary action, and each membrane was subsequently analyzed. FIG. 4A shows capture layer number 10 after probing with a monoclonal antibody against PSA and visualization by enhanced chemiluminescence (ECL). Samples 1 (purified PSA) and 5 (normal prostate tissue) show a positive signal, which indicates that PSA has been successfully captured. Samples 2 (normal lung), 3 (lung tumor), 4 (esophageal tumor), and 6 (breast cancer) do not contain PSA and are appropriately negative.

A location of each of the samples that was placed on the top layer was substantially preserved and reproduced on the membranes through which the samples were transferred. Their substantial retention of spatial relationship conveniently allows the resulting patterns to be correlated with the original specimens.

EXAMPLE 3

Specificity of PSA Capture

Figure 4B:
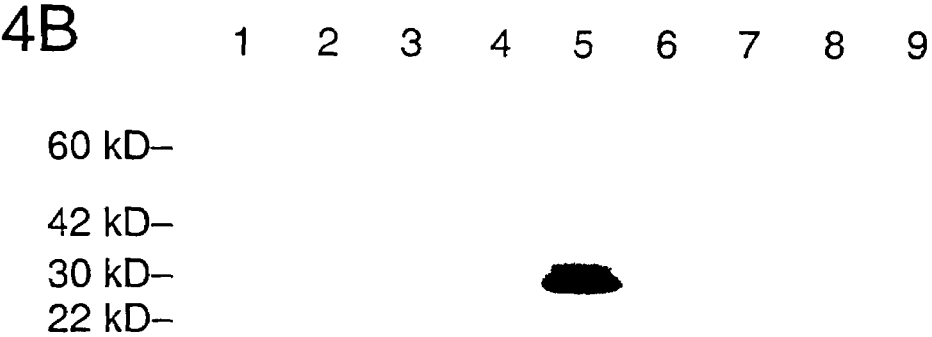
FIG. 4B is a diagram illustrating the staining pattern obtained when each individual layer of a stack of ten LES layers was analyzed separately by electrophoresis for PSA.

To show the specificity of the capture process, a single sample of prostate tissue was solubilized and transferred through a set of capture layers as described in Example 2 above, except that polyclonal anti-PSA was placed on membrane 5. After the transfer of the prostate tissue through the layers, each membrane was placed in denaturing buffer to remove captured molecules. The proteins recovered from every membrane were subsequently separated by gel electrophoresis (the proteins recovered from layer 1 were run in Lane 1, the proteins recovered from layer 2 were run in lane 2, and so forth) and analyzed by immunoblot using a monoclonal anti-PSA antibody. FIG. 4B shows the results from each of capture layers one through nine. Lane 5 (representing layer 5, linked to anti-PSA) shows a single, distinct PSA band at $M_r$=30,000 (30 kDa). The remaining capture membranes are negative for PSA. This result demonstrates that PSA was captured only on the membrane containing its antibody. Moreover, the single band on the immunoblot indicates that the ECL signal derived from the capture membrane in Example 2 was specific for PSA.

Figure 4C:
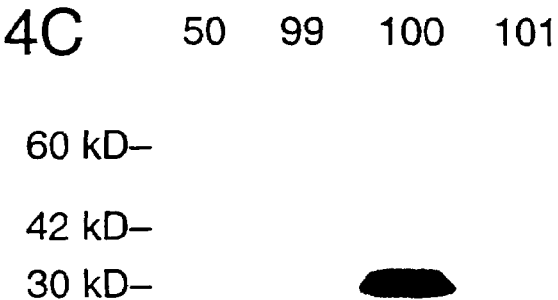
FIG. 4C is a diagram illustrating the staining pattern obtained when each individual layer of a stack of 100 LES layers was analyzed separately by electrophoresis for PSA.

To illustrate the potential of the method for high-throughput analysis, a repeat of the experiment was performed except the tissue was transferred through 101 capture layers with anti-PSA placed on layer number 100. Successful and specific capture of PSA is shown in FIG. 4C. Only lane 100 (representing layer 100, linked to anti-PSA) shows a single, distinct PSA band at $M_r$=30,000 (30 kDa). The remaining capture membranes are negative for PSA. The specific and selective capture observed after transfer through this large number of layers indicates that it is possible to utilize layered expression scanning for the simultaneous measurement of hundreds, thousands, or even tens of thousands of molecular species, by providing different capture agents in different layers.

EXAMPLE 4

Capture of Active Enzymes

Figure 4D:
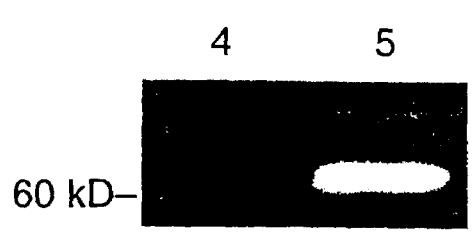
FIG. 4D is a diagram illustrating the gel zymography results obtained after mmp-2 was transferred through 100 LES layers.

To demonstrate the ability of layered expression scanning to capture and analyze active enzymes a repeat of the ten layer experiment described above in Example 3 was performed, except the anti-PSA antibody that was linked to capture layer 5 was replaced by an antibody against matrix metalloproteinase-2 (MMP-2). Purified MMP-2 protein was transferred through the capture layers, and each membrane was subsequently analyzed by gelatin zymography. FIG. 4D shows successful capture of MMP-2 represented by a single band at $M_r$=72,000 (72 kDa) in lane 5 that corresponds to capture layer 5. All other lanes, corresponding to layers not containing anti-MMP-2 antibodies, were negative for MMP-2.

EXAMPLE 5

Selective and Specific Capture of Nucleic Acids

Figure 5:
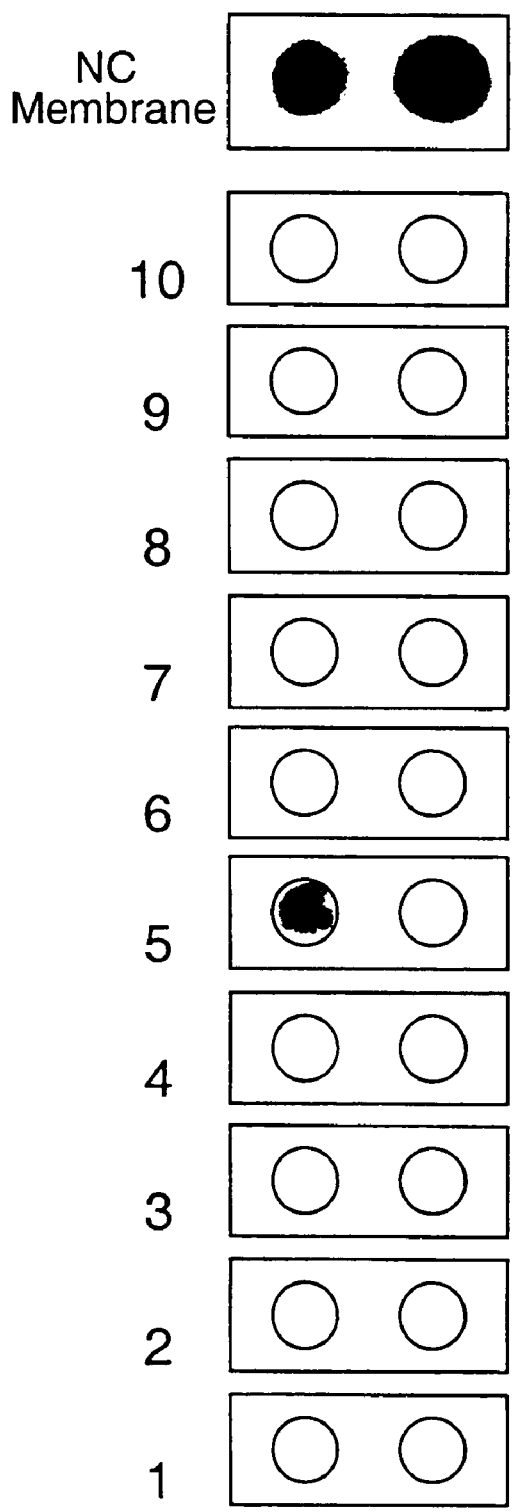
FIG. 5 shows the autoradiograms obtained for ten LES layers and a nitrocellulose membrane after radiolabeled PCR products from pov1 and β-actin transcripts were transferred as discrete spots through ten capture layers. Layer 5 was linked to a plasmid containing the entire pov1 cDNA. A non-blocked nitrocellulose membrane (shown at the top) was used to bind the noncaptured transcripts after they traversed the set of layers.

This example demonstrates the ability of layered expression scanning to analyze nucleic acids. $^{32}$P-labeled PCR products (200 bp) were amplified from plasmids containing cDNAs of the POV1 (PB39, NCI) and β-actin (Clonetech, Palo Alto, Calif.) genes, respectively. The radiolabeled PCR products were excised from an agarose gel, and 5% of each product was placed in discrete 4 mm spots as described for the tissue samples in Example 2. The PCR products were transferred through 10 capture layers overnight by capillary transfer using 6×SSC. In this experiment, the capture layers consisted of ultrathin (<50 μm) 2% agarose gels. Capture layer five contained a plasmid containing the entire cDNA for the POV1 gene. During preparation of layer 5, the POV1 cDNA-containing plasmid was added to the agarose prior to gel polymerization at a final concentration of 30 ng/μL. A nonblocked nitrocellulose membrane was used to bind the noncaptured POV1 and β-actin PCR products after they traversed the membrane set. After transfer, the layers were separated and visualized by X-OMAT radiography. FIG. 5 shows successful and selective capture of POV1 cDNA in layer 5, while the actin PCR product moved through the entire set of layers and was not captured until it reacted the nonblocked nitrocellulose layer.

EXAMPLE 6

Transfer of Intact Tissue Sections

The Examples above show the feasibility of layered expression scanning to analyze tissue samples after they have been appropriately procured and solubilized. Layered expression scanning may also be utilized to analyze intact tissue sections. If an intact tissue section is used as the sample, it is possible to correlate the two-dimensional architecture of the tissue section with the two-dimensional pattern of cellular components localized in particular capture layers following transfer.

To demonstrate the retention of the two-dimensional architecture of a tissue section, 10 μm thick whole-mount cryostat sections of human prostate from radical prostatectomy specimens were placed on top of either a ten-layer or a one hundred-layer agarose gel set. The intact tissue section was transferred through the layers by capillary fluid movement overnight at room temperature to a 1.75-square inch, 0.45 μm pore size nitrocellulose membrane (Schleicher and Schuell). After transfer of the tissue sections, the nitrocellulose membranes were probed with an antibody against cytokeratin (Sigma 1:1000 dilution) to selectively identify epithelial elements and were visualized by ECL according to the recommendations of the manufacturer (Pierce).

Retention of the basic organization of the tissue section throughout the transfer process is demonstrated in FIGS. 3 A–D by comparing the transferred sections (FIG. 3A and FIG. 3C) with a hematoxylin and eosin (H&E) stained slide of an adjacent recut section. The overall architecture of the transferred sections is highly similar to the corresponding H&E stained slides, and the location of individual glandular epithelial elements within the tissue sections can be determined. Thus, layered expression scanning can be used for analyzing intact tissue sections while retaining a correspondence between the two-dimensional architecture of the tissue section and the two-dimensional position of components transferred to the capture layers. Single cell-level of resolution will permit individual cells to be analyzed for the presence of particular molecules. For example, in prostate cancer, all of the individual normal glands premalignant foci, and high- and low-grade tumor glands could be simultaneously analyzed, as well as important sub-populations, such as tumor glands, that are invading through the prostate capsule. Alternatively, microscopic structure level resolution could allow localization of particular proteins to individual subcellular organelles.

EXAMPLE 7

Layered Expression Scanning Membranes

Membranes and gels useful for creating identification and capture layers as utilized in the Examples may have one or more of the following properties. First, the membranes or gels are able to immobilize individual identification or capture molecules (e.g. antibodies, nucleic acids, and dyes). Second, the membranes or gels permit cellular components transferred from a sample to efficiently traverse the set of layers and accumulate or react in the appropriate layer. Third, the membranes or gels facilitate transfer with minimal loss of the two-dimensional relationship of the biological sample(s).

Particular examples of materials appropriate for constructing a set of layers for layered expression scanning include nitrocellulose membranes, derivatized nitrocellulose membranes, high concentration agarose gels, low concentration agarose gels, high concentration polyacrylamide gels, a low concentration polyacrylamide gel, and membranes, such as porous membranes like nitrocellulose paper. Low concentration agarose is from about 0.1 to about 3%, while high concentration is above about 3%. Low concentration acrylamide is about 2% to about 20%, while high concentration is above about 20%.

Individual layers may also be composites of two or more membranes or gels. For example, thin polymer membranes, such as polar polymer membranes, for instance polyester membranes, may be combined with nitrocellulose membranes or agarose or polyacrylamide gels to form composite layers for layered expression scanning.

In a particular embodiment, the composite membrane is formed as follows. A thin (10 µm) polyester membrane is used as a backbone layer. The polyester membrane is then coated with a soluble polymer material, such as 2% agarose, to form an ultrathin (<1 µm) layer covering the polyester backbone. A capture molecule (e.g., an antibody or nucleic acid) is added to the polymer material prior to its addition to the polyester backbone. After the polymer is coated on the backbone, it forms a gel and irreversibly traps the capture molecule within the gel structure. The polyester backbone/polymer gel composite containing the capture molecule may then be used as a layered expression scanning capture membrane. Experiments have demonstrated that such composite membranes are highly efficient at meeting the criteria described above. A particular advantage of the composite membranes is that the polymer gel that is coated on the polyester backbone serves as a "contact substance" between each of the layers, thereby permitting efficient transfer of biomolecules with minimal loss of correspondence with the two-dimensional architecture in the sample.

EXAMPLE 8

Determination of the Binding Status or Binding Partner of a Molecule of Interest during Tumor Progression Different tumor cell populations, distinguished by the stage of tumor progression, are separately collected using laser microdissection techniques as described by Emmert-Buck et al. (1997). Each different cell population is placed in its own location within a sample gel, as described above in Example 1. The sample gel is placed on a multi-layer substrate, containing at least one layer cross-linked with antibodies against one or more known binding partners of the molecule of interest. The molecules could be treated with a cross-linking agent, thus binding partners will remain in the state they are in at the time of the preparation of the cryostat during transfer. After transfer of the components of the cell populations through the substrate layers as described above, the layers are separated and the molecules of interest are run on a gel and probed by the capture antibody. Thus, this experiment shows whether or not a molecule of interest is bound or free at various stages of tumor development by determining the molecular weight of the species when the tissue sample is prepared.

In order to search for new binding partners, the experiment is performed as described above for binding status without the pre-transfer cross-linking. After transfer of the cellular specimen, mass spectrometry can be used to determine the identity of proteins that are captured along with the protein of interest. After separation from the capture molecule and isolation in a gel, MS-MS (mass spectrometry-mass spectrometry) sequencing can identify the proteins recovered from relatively few numbers of microdissected cells as described in Huang et al. (1999).

EXAMPLE 9

Comparative Expression Between Normal and Diseased Cell Populations

LES can be used as an "open system" to search for disease associated molecular alterations in tissue samples. In this example, normal and diseased cell samples are placed within the sample gel as described in Example 1. The information molecules cross-linked on the membrane layers can be antibodies, peptides, or DNA sequences for either known proteins, or libraries of ssDNA or mRNA. Large numbers of capture molecules are simultaneously used to analyze the comparative expression between normal and diseased cell populations of the targets of the capture molecules. The samples tested can be derived from one or multiple patients. Once a protein or nucleic acid is shown to be expressed differently in normal and diseased cells, its identity can be determined by the capture molecule to which it binds. This identity can be confirmed using standard sequencing techniques, or such sequencing techniques can be used initially to determine whether the target of the capture molecule is unknown.

EXAMPLE 10

Determination of the Structure of a Protein of Interest During Tumor Progression Different cell populations, distinguished by the stage of tumor progression, are separately collected using laser microdissection techniques as described by Emmert-Buck et al. (1996). Each cell population is placed in its own location within a sample gel, as described above in Example 1. The sample gel is placed on a substrate, containing at least one membrane cross-linked with polyclonal antibody against tumor suppressor protein. After transfer of the components of the cell populations through the substrate layers, the membranes are separated and the anti-tumor suppressor protein membrane, with its captured molecules, is probed with two differentially labeled monoclonal antibodies that recognize different regions of the tumor suppressor protein. One antibody is specific for the N-terminus of the protein, and the other is specific for the C-terminus of the protein. By comparing the presence or absence of the N- or C-terminus of the protein at various stages of tumor progression, this investigation can detect if the tumor suppressor protein has been truncated at some point during tumor development. Mutation is one example of an event that could lead to protein truncation. Such alterations in proteins during the transition between normal and tumor cells is known to occur, for example in the adenomatous polyposis coli (APC) tumor suppressor gene product, as reported by Smith et al. (1993).

EXAMPLE 11

Use of Differential Transfer from the Sample Gel

Initial placement of the tissue specimen into a high concentration gel limits migration to relatively small proteins. Alternatively, low concentration gels allow larger molecules to be transferred and analyzed. In the normal prostate, PSA is localized exclusively within epithelial cells, whereas in tumors PSA is able to enter the stroma and is bound by alpha-1 anti-chymotrypsin (ACT) as described by Chen et al. (1995). PSA and ACT form an enzyme-inhibitor complex with a significantly larger aggregate molecular weight than PSA alone. By altering the characteristics of the gel into which the tissue sample is placed, it is possible to separately analyze PSA and PSA-ACT complex in tumors. There is selective membrane capture of PSA after placing a prostate tumor section into a 2% agarose gel. However, when the concentration of the gel is reduced to 0.5%, both PSA and PSA-ACT migrate through the membranes and are captured. Alteration of experimental conditions to effect molecular migration can allow investigators to customize experiments as needed for particular objectives. For example, study of subcellular molecular profiles may be performed by utilizing transfer buffers with and without detergents to selectively mobilize soluble or membrane-bound proteins.

EXAMPLE 12

Automated Expression Scanning

The layered expression scanning of the present invention can also be used in association with an automated laboratory instrument capable of multiple applications. For example, the capture layers in the present prototype system are replaced by thin transparent membranes such that several thousand stacked layers will cumulatively be only a few millimeters in thickness. Thus, the total migration distance of the tissue sample during transfer and detection or immobilization is minimal, thereby optimizing the cellular resolution of the system. In this application the tissue sample, wash buffers, and fluorescently labeled secondary detection molecules are transferred through the intact membrane set, thus obviating the need to separate and individually process each capture layer. The sample, wash buffers and fluorescently labeled secondary detection molecules may be transferred into the stacked layers either in the same direction as the sample components are conducted through the stacked layers or in another direction, such as in the reverse direction or along the direction of the layers themselves. The intact membrane set is then analyzed by confocal fluorescence microscopy, and the expression data of each individual layer is determined and overlayed with the high quality histological image of the tissue section. The approach was demonstrated in an experiment similar to that shown in FIG. 4, in which each of the detection reagents were transferred through the capture membranes while the membranes remained as an intact set. Successful capture and analysis occurred.

In yet another embodiment, the set of capture layers may be utilized repeatedly to produce expression scans by washing the stacked layers with a denaturing buffer between scans to remove captured molecules. Suitable buffers for this purpose include buffers containing denaturants, such as detergents or urea, and salts, such as sodium chloride, at concentrations that are sufficient to remove captured molecules from the stacked layers. A particular example of a suitable denaturing buffer is a buffer containing 1% sodium dodecyl sulfate (SDS) and 500 mM sodium chloride. Other denaturing buffer systems are known in the art and their suitability for use with automated expression scanning can be determined by analyzing the layers for the continued presence of bound molecules after they are washed with a particular denaturing buffer system.

In another approach, the capture membranes will be separable and processed individually after tissue transfer. The separated membranes may then be studied beyond measurement of expression levels of individual molecules. For example, mass spectrometry can be used to identify binding partners which are "co-captured" along with targeted proteins.

EXAMPLE 13

Analysis of Individual Cloned Biomolecules

The layered expression scanning (LES) methods can be used to analyze for individual cloned biomolecules, such as messenger RNAs recovered from a cell population and cloned into bacteria using standard methods.

In a particular embodiment, the bacteria are plated on media and individual colonies are grown in the presence of a labeled nucleotide. Individual colonies are then placed on top of an LES device and the nucleic acids from each colony are transferred through a set of LES layers such as those described in Example 5 above and where each LES layer contains an individual cDNA clone. The identity of the cDNA in all bacterial colonies is simultaneously determined by analyzing for the presence or absence of hybridization on each capture membrane after the cloned DNA has traversed the LES layer set. One application of this particular method is to perform high-throughput gene expression analysis of a given cell population by determining the identity of a large number of bacterial clones derived from a particular cells messenger RNA population.

EXAMPLE 14

Analysis of the Genomic Content of Cells

The layered expression scanning method may be used to analyze the genomic DNA content of individual cells or cells within a tissue section. One example of this application is as follows.

DNA from a series of cell lines is purified, labeled with a "tagged" (radiolabeled or fluorescently labeled) nucleotide and placed in a grid on a membrane on top of the LES device, such as described above in Example 2. In this particular embodiment, each of the LES layers contains a specific genomic DNA clone. The DNA samples are transferred through the LES layers such that the DNA gragments from the cell samples specifically hybridize to the LES layer that contains the corresponding genomic clone. The LES layers are then analyzed (by radiography or fluorescence) to provide a quantitative measure of the amount of DNA in each cell sample at each genomic locus included in the LES layer set. This application would be useful in determining the specific regions of DNA (and associated genes) that are amplified or deleted in a series of cell lines.

Although many of the foregoing examples have been described in association with a layered substrate, in which discrete or separable layers extend successively transverse to the path of movement of the material being analyzed, these same principles can be applied to other configurations of the substrate. For example, layers can be arranged substantially parallel, or at some other angular relationship, to the path of movement. In other embodiments, each layer may be subdivided into multiple regions, each with a different capture molecule, which are capable of producing more complex patterns that can be recognized by the user or image processing software. Each of the regions can extend in any desired shape throughout the layer, which can extend in any direction relative to the direction of movement of the sample through the substrate. However, in particularly useful embodiments, the different regions are transverse to the direction of movement to maintain a spatial correspondence between a surface of the substrate to which the specimen is applied, and the region which captures a molecule of interest.

Although disclosed embodiments examine a pattern of interaction in successive layers which correspond to positions on a surface of the substrate, any pattern that conveys information about the molecular content of the specimen may be used. With particularly complex patterns (of the type that may be generated by multiple different types of capture molecules in each layer, in regular or irregular patterns, that may extend to different depths of the substrate), pattern recognition software is particularly effective to store and compare patterns.

In view of the many possible embodiments to which the principles of this invention may be applied, it should be recognized that the illustrated embodiments are only particular examples of the invention, and should not be taken as a limitation on the scope of the invention. Rather, the scope of the invention is defined by the following claims, and the invention includes all that comes within the scope and spirit of these claims.

REFERENCES

W. Bonte, *Acta histochem.* 62: 68–77 (1978).
Z. Chen et al., *Clin. Chem.* 41: 1273–82 (1995).
M. Emmert-Buck et al., *Science* 274: 998–1001 (1996).
M. Inczedy-Marcsek et al., *Acta Histochem. Supp.* 36: S377–94 (1988).
T. Grogan, *Am. J. Clin. Pathol.* 4(Supp. 1): S35–8 (1992).
Z. Huang et al., *Anal Biochem* 268:305–17 (1999).
L. Jin and R. Lloyd, *J. Clin. Lab. Anal.* 11:2–9 (1997).
J. Kononen et al., *Nat. Med.* 4: 844–847 (1998).
I. Lefkovits et al. (eds.), *Immunology Methods Manual* (1996).
J. Lindner et al., *Naturwissenschaften* 43: 201 (1956).
V. Neuhoff, *Electrophoresis* '79 (1980).
C. Saravis et al., *J. Immun. Meth.* 29:97–100 (1979).
U. Schumacher et al. (1990), *Histochem. J.* 22:433–438 (1990).
U. Schumacher and D. Trudrung, *Anal. Biochem.* 194: 256–58 (1991).
M. Schena et al., *Science* 270: 467–469 (1995).
K. Smith et al., *Proc. Natl. Acad. Sci.* 90: 2846–2850 (1993).
P. van der Sluis et al., *Electrophoresis* 9: 654–66 (1988).
L. Zhang et al., *Science* 276: 1268–1272 (1997).
S. Zucker et al., *Clin. Exp. Metastasis* 12:13–23 (1994).

I claim:

1. A method of analyzing a biological specimen, comprising:
    placing the biological specimen on a substrate with a plurality of different layers, wherein the plurality of different layers of the substrate contain different identification molecules that interact with different components from the biological specimen; and
    transferring components from the biological specimen through the plurality of different layers under conditions that allow the components to interact different identification molecules in the different layers of the substrate, wherein a two-dimensional architecture of the biological specimen is preserved throughout the transfer such that the transferred components interacting with the different identification molecules produce a pattern on each of the different layers, and wherein the pattern on each layer corresponds to the location of the components from the biological specimen,
    thereby analyzing the biological specimen.

2. The method of claim 1, wherein the biological specimen is a cellular specimen.

3. The method of claim 2, wherein the layers are contiguous, and components from the cellular specimen are transferred through the plurality of different layers of the substrate by capillary action of the substrate.

4. The method of claim 2, wherein the layered substrate comprises contiguous porous layers that exert capillary pressure on the cellular specimen.

5. The method of claim 2, wherein the components from the cellular specimen are transferred through the plurality of different layers of the substrate by electrophoresis.

6. The method of claim 2, wherein the components maintain a cellular architecture of the specimen as the components are transferred through the layers of the substrate.

7. The method of claim 6, further comprising correlating interaction between different identification molecules and the components from the cellular specimens, with a cellular architecture of the specimen.

8. The method of claim 2, further comprising placing multiple different discrete cellular specimens on a surface of the substrate, wherein a correspondence between a position on the surface of the substrate and a position in the substrate to which the component is transferred is maintained between the multiple discrete cellular specimens and particular transferred components.

9. The method of claim 8, wherein at least 20 different cellular specimens are placed on the surface of the substrate.

10. The method of claim 2, wherein the cellular specimen is a section of a tissue specimen.

11. The method of claim 10, wherein the cellular specimen is a section of a tumor.

12. The method of claim 2, further comprising correlating a pattern of interactions of different identification molecules in the plurality of different layers of the substrate with a component having a known identity.

13. The method of claim 2, wherein there are at least 10 layers of the substrate.

14. The method of claim 13, wherein there are at least 100 layers of the substrate.

15. The method of claim 2, wherein the layers of the substrate have a thickness of at least about 25 µm.

16. The method of claim 2, wherein the identification molecules are antibodies that interact with the components from the cellular specimen.

17. The method of claim 2, wherein the identification molecules interact with different cellular regions of the cellular specimen, and interaction of the identification molecules is correlated with a region of the cellular specimen.

18. The method of claim 2, wherein the cellular specimen is placed on a surface of the layered substrate prior to transferring components from the cellular specimen through the substrate.

19. The method of claim 2, wherein the specimen is treated, prior to transferring components from the cellular specimen through the layers, to selectively transfer components through the layers.

20. The method of claim 19, wherein the specimen is placed on a surface of the layered substrate in a gel, and a concentration of the gel is varied to selectively transfer components of different molecular size.

21. The method of claim 20, wherein a high concentration gel is used to selectively transfer proteins of a relatively smaller molecular size.

22. The method of claim 2, comprising identifying the components of the specimen by determining which identification molecules the components interact with.

23. The method of claim 22, further comprising interacting an identified component with a second identification molecule, to determine whether the identified component is associated with an other component.

24. The method of claim 23, wherein the cellular specimen is a tumor specimen, and the identified component is an intact protein, and identification of the other component is used to determine whether a second protein is associated with the protein in the tumor.

25. The method of claim 24, wherein multiple tumor specimens are placed on the substrate, and components of the multiple tumor specimens are simultaneously separately transferred through the substrate.

26. The method of claim 25, wherein the multiple tumor specimens are specimens of a particular type of tumor at different stages of tumor progression.

27. The method of claim 26, wherein the multiple tumor specimens are specimens of a tumor from a particular subject at different stages of tumor progression in that subject.

28. The method of claim 2, wherein the cellular specimen is obtained by dissecting a cell population of interest from a larger cell population.

29. The method of claim 28, wherein dissecting a cell population of interest comprises laser capture microdissection of the cell population.

30. The method of claim 2, wherein the cellular specimen comprises a cell lysate from a cell population of interest.

31. The method of claim 2, wherein one or more of the layers is an electrically conductive layer.

32. The method of claim 31, wherein the layers are separable, and are separated after transferring the components from the cellular specimen, for individualized identification of the components from the cellular specimen retained in each separated layer.

33. The method of claim 31 wherein the each layer is selected from the group consisting of a high concentration agarose gel, a low concentration agarose gel, a high concentration polyacrylamide gel, a low concentration polyacrylamide gel, and a membrane.

34. The method of claim 2 wherein the identification molecules are molecules selected from the group consisting of antibodies, nucleic acids, peptides, receptors, and ligands.

35. The method of claim 2 wherein the identification molecule comprises a capture molecule which retains a component from the cellular specimen in the layer, the method further comprising exposing the identification molecule to a detection molecule that associates with a combination of the capture molecule and the component of the sample, or associates with a region of the component different than a region that is recognized by the identification molecule.

36. The method of claim 35, wherein the component is a protein, the identification molecule recognizes a first domain of the protein, and the detection molecule recognizes the different region of the protein.

37. The method of claim 36, wherein the detection molecule is selected from the group consisting of antibodies, nucleic acids, peptides, receptors, ligands and stains.

38. The method of claim 2, wherein the identification molecules capture components of the transferred components in relative abundance to a quantity of the components in the cellular specimen, and provide a quantitative indication of the relative abundance of the components in the cellular specimen.

39. The method of claim 2, wherein the cellular specimen is selected from the group consisting of a tissue section, cultured cells, and a cytology sample.

40. The method of claim 1, wherein the transferred components that interact with the different identification molecules comprise intact proteins or intact nucleic acid molecules that have not been subjected to proteolytic or nucleolytic reactions prior to transfer through the different layers of the substrate.

41. The method of claim 1, further comprising capturing a component of the components from the cellular specimens, and performing mass spectroscopy sequencing to identify the captured component.

42. The method of claim 2, wherein transferring components from the biological specimen through the layered substrate produces a three dimensional matrix, wherein a surface of the substrate on which the biological specimen is placed provides a two dimensional matrix, and a third dimension is provided by transfer of components from the biological specimens through the plurality of different layers, wherein there is an identifiable correspondence between a position of the component from the biological specimen in the two dimensional matrix and a position of the transferred components in the three dimensional matrix.

43. A method of analyzing a cellular specimen, comprising:

provided a substrate comprising a plurality of different layers having contiguous faces, each layer including a corresponding capture molecule capable of interacting with and capturing a component from the cellular specimen; applying the cellular specimen to a face of the substrate, and transferring intact components of the specimen through the contiguous faces of the different layers, wherein a two-dimensional architecture of the cellular specimen is preserved throughout the transfer such that the transferred components reacting with the capture molecule form a pattern on each of the different layers, and wherein the pattern on each layer corresponds to the location of the components from the cellular specimen; and correlating a pattern of capture in the different layers with information about the cellular specimen.

44. The method of claim 43, wherein the capture molecule captures the component in an amount that corresponds to a quantity of the component in the cellular specimen.

45. The method of claim 43, wherein the intact components comprise one or more of proteins or nucleic acids that have not been subjected to a proteolytic or nucleolytic processing step.

46. The method of claim 43, wherein applying the cellular specimen to a face of the substrate comprises applying multiple different cellular specimens to the face of the substrate.

47. The method of claim 43, wherein the pattern of capture comprises a three dimensional matrix, in which a pattern of the cellular specimen applied to the face of the substrate forms a two dimensional matrix, and a pattern of capture in the different layers forms a third dimension, wherein there is a correspondence between the two dimensional matrix and the third dimension, such that the pattern of capture can be correlated to specific cellular architecture in the cellular specimen.

48. The method of claim 43, wherein transferring intact components of the specimen comprises introducing an electrical current through the contiguous faces of the substrate, so that the current flows transverse to the plurality of different layers.

49. The method of claim 48, wherein the plurality of different layers comprises a plurality of contiguous electrically conductive gels through which the electrical current is conducted.

50. The method of claim 43, wherein transferring intact components of the specimen comprises transferring by capillary action.

51. The method of claim 50, wherein the plurality of different layers comprise contiguous nitrocellulose layers that exert capillary pressure on the cellular specimen.

52. The method of claim 1, wherein the transferred components that interact with the different identification molecules comprise intact proteins or intact nucleic acid molecules that have not been subjected to proteolytic or nucleolytic reactions prior to transfer through the different layers of the substrate.

53. The method of claim 1, further comprising capturing a component of the components of the biological specimens, and performing mass spectroscopy sequencing to identify the captured component.

54. The method of claim 1, wherein transferring components from the biological specimen through the layered substrate produces a three dimensional matrix, wherein a surface of the substrate on which the biological specimen is placed provides a two dimensional matrix, and a third dimension is provided by transfer of components from the biological specimens through the different layers, wherein there is an identifiable correspondence between a position of the component from the biological specimen in the two dimensional matrix and a position of the transferred components in the three dimensional matrix.

55. The method of claim 2, wherein the layers are separable, and are separated after transferring the components from the cellular specimen, for individualized identification of the components from the cellular specimen retained in each separated layer.

56. The method of claim 43, wherein the layers are separable, and are separated after transferring the components from the cellular specimen, for individualized identification of the components from the cellular specimen retained in each separated layer.

57. The method of claim 1, wherein the pattern on each layer is further informative about the quantity of the components in the biological specimen.

* * * * *